(12) United States Patent
Sasai

(10) Patent No.: US 9,006,693 B2
(45) Date of Patent: Apr. 14, 2015

(54) ENERGY DEGRADER AND CHARGED PARTICLE IRRADIATION SYSTEM INCLUDING THE SAME

(71) Applicant: Sumitomo Heavy Industries, Ltd., Tokyo (JP)

(72) Inventor: Kenzo Sasai, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 13/944,468

(22) Filed: Jul. 17, 2013

(65) Prior Publication Data

US 2013/0299721 A1   Nov. 14, 2013

(30) Foreign Application Priority Data

Jan. 18, 2011 (JP) .................................. 2011-008209
Jan. 13, 2012 (WO) .................. PCT/JP2012/050633

(51) Int. Cl.
*A61N 5/10* (2006.01)
*G21K 1/10* (2006.01)
*G21K 5/04* (2006.01)
*H05H 7/00* (2006.01)

(52) U.S. Cl.
CPC ............ *A61N 5/1077* (2013.01); *A61N 5/1043* (2013.01); *A61N 2005/1087* (2013.01); *A61N 2005/1095* (2013.01); *H05H 2007/004* (2013.01); *G21K 1/10* (2013.01); *G21K 5/04* (2013.01)

(58) Field of Classification Search
CPC .............. A61N 2005/1087; A61N 2005/1095; A61N 5/1043
USPC ............................................ 250/492.3, 505.1
See application file for complete search history.

(56) References Cited

U.S. PATENT DOCUMENTS 6,433,336 B1 * 8/2002 Jongen et al. ................. 250/305
2006/0192146 A1 * 8/2006 Yanagisawa et al. ...... 250/492.1

FOREIGN PATENT DOCUMENTS

| JP | 07-057900 A | 3/1995 |
| JP | 2002-533888 A | 10/2002 |
| JP | 2006-034582 A | 2/2006 |
| WO | WO-00/38486 A1 | 6/2000 |

* cited by examiner

*Primary Examiner* — Jack Berman
*Assistant Examiner* — Kevin Chung
(74) *Attorney, Agent, or Firm* — Rader, Fishman & Grauer PLLC

(57) ABSTRACT

An energy degrader includes: a damping unit that attenuates energy of incident charged particles and has a thickness changing stepwise or continuously according to a position of a two-dimensional coordinate system within a plane crossing a traveling direction of charged particles; and a driving unit that performs translational driving of the damping unit in first and second axial directions that are directions of two axes crossing each other in the two-dimensional coordinate system.

5 Claims, 4 Drawing Sheets

ENERGY DEGRADER AND CHARGED PARTICLE IRRADIATION SYSTEM INCLUDING THE SAME

INCORPORATION BY REFERENCE

Priority is claimed to Japanese Patent Application No. 2011-008209, filed Jan. 18, 2011, and International Patent Application No. PCT/JP2012/050633, the entire content of each of which is incorporated herein by reference.

BACKGROUND

1. Technical Field

The present invention relates to an energy degrader to attenuate the energy of charged particles and a charged particle irradiation system including the same.

2. Description of the Related Art

Equipment that irradiates a patient with charged particles, such as proton beams, to perform cancer treatment is known. This kind of equipment includes a cyclotron to accelerate ions (charged particles) generated by an ion source, a transport line to transport the charged particles accelerated by the cyclotron, and a rotatable irradiation device (rotating gantry) to irradiate the patient with charged particles from an arbitrary direction.

In a particle beam irradiation device disclosed in the related art, a depth-direction position of the charged particle beam that reaches the inside of an irradiation object is controlled by attenuating the energy of the charged particle beam accelerated by a synchrotron (accelerator) using a range shifter. This range shifter is formed so as to have a thickness changing in a stepwise manner, and controls the position in a depth direction by making the charged particle beam pass through a specific stage of the stages formed in a stepwise manner.

In the technique disclosed in the related art, the attenuation of energy is changed by changing the passing position of the charged particle beam by driving the range shifter in one axial direction.

SUMMARY

According to an embodiment of the present invention, there is provided an energy degrader including: a damping unit that attenuates energy of incident charged particles and has a thickness changing stepwise or continuously according to a position of a two-dimensional coordinate system within a plane crossing a traveling direction of charged particles; and a driving unit that performs translational driving of the damping unit in first and second axial directions that are directions of two axes crossing each other in the two-dimensional coordinate system.

DETAILED DESCRIPTION

Figure 1:
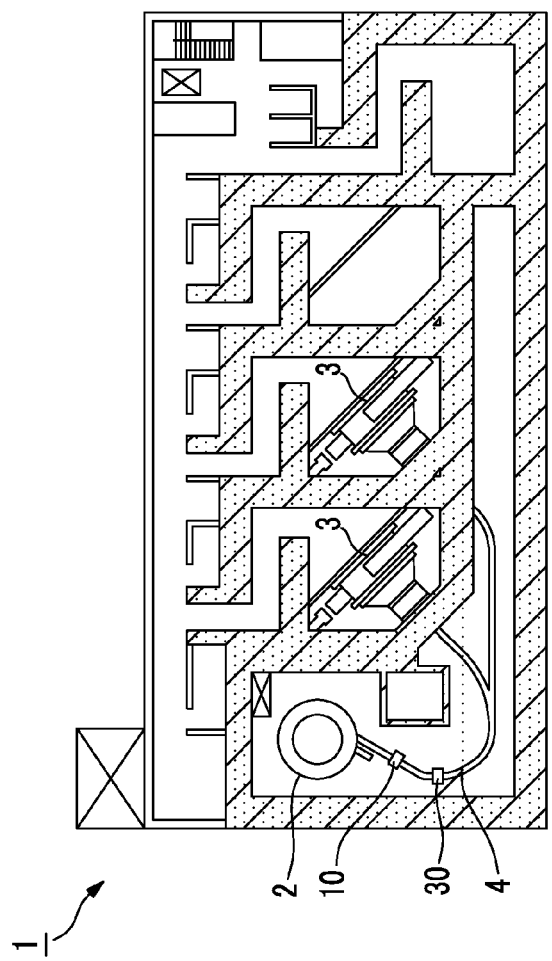
FIG. 1 is a layout diagram of a particle beam therapy system according to an embodiment of the present invention.

The synchrotron disclosed in the related art is configured to be able to change the energy of the accelerated charged particles, but it is very difficult to adjust the energy of the extracted charged particles in the cyclotron itself. When adjusting the energy of the extracted charged particles in the cyclotron, it is necessary to change the magnitude of the magnetic field generated by the electromagnet provided in the cyclotron. However, when changing the magnitude of the magnetic field, it is not possible to extract charged particles with desired energy unless other devices (for example, the frequency of the current supplied to the D electrode) in the cyclotron are precisely adjusted. Since this requires a lot of time and effort, there is a problem in that this is not practical.

In addition, when applying the above-described method of driving the range shifter in the one axial direction to the device that attenuates the charged particles accelerated by the cyclotron, the range shifter becomes long in the one axial direction. This leads to an increase in the size of the device. Therefore, an energy degrader capable of reducing the size of the device has been required.

It is desirable to provide an energy degrader capable of reducing the size of a device and a charged particle irradiation system including the energy degrader.

In the energy degrader according to the embodiment of the present invention, a damping unit having a thickness changing stepwise or continuously is disposed in a two-dimensional manner on the plane crossing the traveling direction of charged particles. In addition, since the energy degrader is configured to include a driving unit that performs translational driving of the damping unit in the first and second axial directions crossing each other in the two-dimensional coordinate system, it is possible to take advantage of the damping unit in which portions having different thicknesses are disposed in a two-dimensional manner. Accordingly, it is possible to reduce the maximum size of the appearance of the damping unit compared with a method of driving the damping unit in one axial direction. As a result, it is possible to reduce the size of the device. In addition, since the movement time is shortened by moving the damping unit in the two axial directions simultaneously, it is possible to shorten the adjustment time of the energy attenuation.

Here, it is preferable that directions of two axes perpendicular to each other in the two-dimensional coordinate system be set as the first and second axial directions, the damping unit be a group of a plurality of pieces having different thicknesses, the group include a piece column in which the plurality of pieces are disposed such that the thickness changes sequentially along the first axial direction, and the plurality of pieces be disposed such that the thickness changes sequentially in opposite directions between the adjacent piece columns. In this case, since a plurality of pieces are disposed such that the thickness changes sequentially, it is possible to shorten the adjustment time of the energy attenuation by shortening the moving distance of the damping unit.

In addition, according to another embodiment of the present invention, there is provided a charged particle irradiation system for irradiating charged particles including the energy degrader described above. In addition, the charged particle irradiation system according to the embodiment of the present invention may further include: an accelerator that is disposed before the energy degrader and accelerates the charged particles; an energy selection unit that is disposed after the energy degrader and extracts charged particles of desired energy width selectively from the charged particles having passed through the energy degrader; and an irradiation device that is disposed after the energy selection unit and irradiates the charged particles of the desired energy width extracted by the energy selection unit.

The charged particle irradiation system according to the embodiment of the present invention includes an energy degrader in which a damping unit having a thickness changing stepwise or continuously is disposed in a two-dimensional manner on the plane crossing the traveling direction of charged particles. In addition, since the energy degrader is configured to include a driving unit that performs translational driving of the damping unit in the first and second axial directions crossing each other in the two-dimensional coordinate system, it is possible to reduce the maximum size of the appearance of the damping unit compared with a method of driving the damping unit in one axial direction. As a result, it is possible to reduce the size of the device. In addition, since the movement time is shortened by moving the damping unit in the two axial directions simultaneously, it is possible to shorten the adjustment time of the energy attenuation.

In addition, according to still another embodiment of the present invention, there is provided an energy degrader including: a damping unit that attenuates energy of incident charged particles and has a thickness changing stepwise according to a position of a two-dimensional coordinate system within a plane crossing a traveling direction of charged particles; and a driving unit that rotationally drives the damping unit around a rotary axis extending in the traveling direction and drives the damping unit in a radial direction of a circle having the rotary axis as the center.

In the energy degrader according to the embodiment of the present invention, a damping unit having a thickness changing stepwise is disposed in a two-dimensional manner on the plane crossing the traveling direction of charged particles. In addition, since the energy degrader is configured to include a driving unit that rotationally drives the damping unit around the rotary axis extending in the traveling direction of charged particles and drives the damping unit in the radial direction of a circle having the rotary axis as the center, it is possible to take advantage of the damping unit in which portions having different thicknesses are disposed in a two-dimensional manner. Accordingly, it is possible to reduce the maximum size of the appearance of the damping unit compared with a method of driving the damping unit in one axial direction. As a result, it is possible to reduce the size of the device.

Here, it is preferable that the damping unit be a group of a plurality of pieces having different thicknesses, the group include a piece column in which the plurality of pieces are disposed such that the thickness changes sequentially along the circumferential direction of a circle, and the plurality of piece columns are formed in the radial direction so as to be disposed in a spiral shape having the rotary axis as the center. In this case, since a plurality of pieces are disposed such that the thickness changes sequentially, it is possible to shorten the adjustment time of the energy attenuation by shortening the moving distance of the damping unit.

In addition, according to still another embodiment of the present invention, there is provided a charged particle irradiation system for irradiating charged particles including the energy degrader described above. In addition, the charged particle irradiation system according to the embodiment of the present invention may further include: an accelerator that is disposed before the energy degrader and accelerates the charged particles; an energy selection unit that is disposed after the energy degrader and extracts charged particles of desired energy width selectively from the charged particles having passed through the energy degrader; and an irradiation device that is disposed after the energy selection unit and irradiates the charged particles of the desired energy width extracted by the energy selection unit.

The charged particle irradiation system according to the embodiment of the present invention includes an energy degrader in which a damping unit having a thickness changing stepwise is disposed in a two-dimensional manner on the plane crossing the traveling direction of charged particles. In addition, since the energy degrader is configured to include a driving unit that rotationally drives the damping unit around the rotary axis extending in the traveling direction of charged particles and drives the damping unit in the radial direction of a circle having the rotary axis as the center, it is possible to reduce the maximum size of the appearance of the damping unit compared with a method of driving the damping unit in one axial direction. As a result, it is possible to reduce the size of the device.

Hereinafter, an energy degrader and a charged particle irradiation system including the energy degrader according to preferred embodiments of the present invention will be described with reference to the drawings. In the present embodiment, a case where a charged particle irradiation system is used as a particle beam therapy system will be described.

(Charged Particle Irradiation System)

The particle beam therapy system is applied to cancer treatment, for example, and is an apparatus that irradiates a tumor (irradiation object) in the body of a patient with a proton beam (charged particles).

As shown in FIG. 1, a particle beam therapy system 1 includes a cyclotron (particle accelerator) 2 that generates a proton beam by accelerating ions (cation of hydrogen) generated by an ion source (not shown), a rotating gantry (irradiation device) 3 that irradiates a patient with the proton beam from an arbitrary direction, and a transport line 4 to transport the proton beam generated by the cyclotron 2 (charged particle beam accelerated by the cyclotron) to the rotating gantry 3.

The proton beam accelerated by the cyclotron 2 is transported to the rotating gantry 3 after the path of the proton beam is changed along the transport line 4. A deflection magnet for changing the path of the proton beam is provided in the transport line 4. In addition, an energy degrader 10 (which will be described later in detail) to attenuate the energy of charged particles is provided in the transport line 4.

In addition, in the transport line 4, an energy selection system (ESS) 30 is provided after the energy degrader 10 (on the downstream side of the energy degrader 10). The ESS 30 is for extracting a proton beam of desired energy width selectively from the transported proton beam having a predetermined energy distribution. In the ESS 30, the energy width of the proton beam is selected so as to become a desired range.

The rotating gantry 3 includes a treatment table on which a patient lies and an irradiation unit that irradiates a proton beam toward a patient. Charged particles whose energy has been attenuated by the energy degrader 10 are emitted from the irradiation unit and are irradiated to a target part of the patient.

(Energy Degrader)

Figure 2:
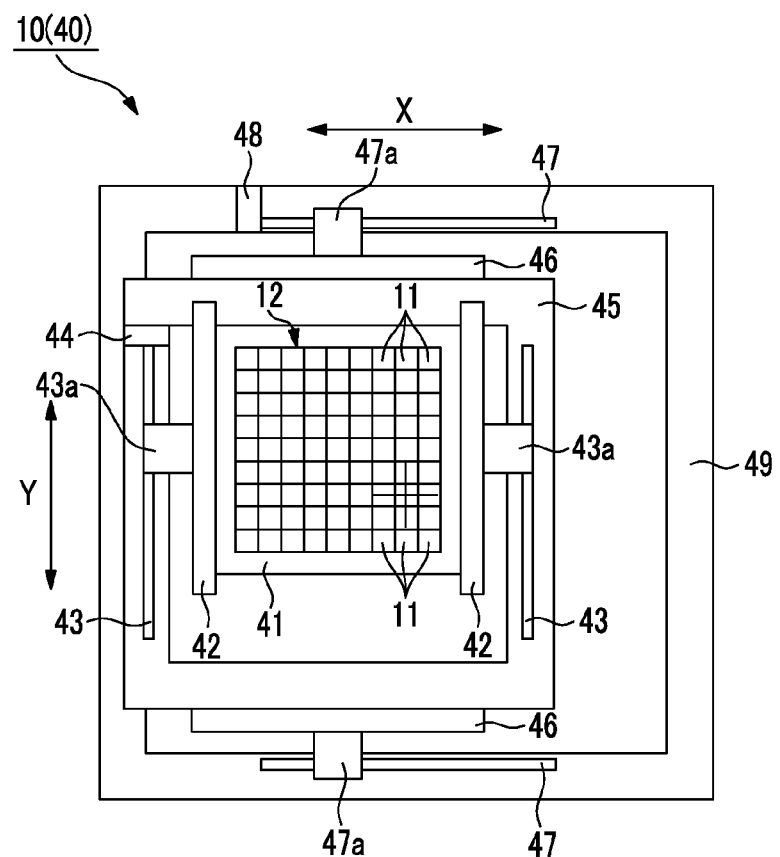
FIG. 2 is a schematic diagram showing an energy degrader according to an embodiment of the present invention.

FIG. 2 is a schematic diagram showing an energy degrader according to the embodiment of the present invention. FIG. 2 shows the energy degrader 10 from the traveling direction of a proton beam B. The energy degrader 10 shown in FIG. 2 is provided on the path of the proton beam B, and is for attenuating the energy of the proton beam B. The energy degrader 10 includes a plurality of damping material pieces 11 to attenuate the energy of the proton beam B transmitted therethrough. As examples of the material of the damping material piece 11, carbon (C) and beryllium (Be) can be mentioned.

Here, the plurality of damping material pieces 11 have different thicknesses, and are disposed in a two-dimensional manner in a plane crossing the proton beam B. For example, as the plurality of damping material pieces 11 disposed in a two-dimensional manner, nine damping material pieces 11 are disposed in a first axial direction X (horizontal direction in the drawing), and nine damping material pieces 11 are disposed in a second axial direction X (vertical direction in the drawing). A group of the plurality of damping material pieces 11 forms a damping unit 12 having a different thickness according to the position of the two-dimensional coordinate system having first and second axes X and Y perpendicular to each other. In addition, the first and second axes X and Y may cross each other, and do not necessarily need to be perpendicular to each other.

Figure 4A:
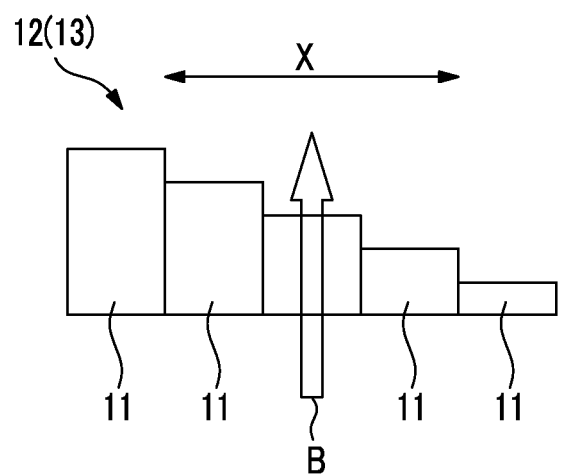
FIGS. 4A and 4B are side views showing the shape of a damping unit in the thickness direction.
Figure 4B:
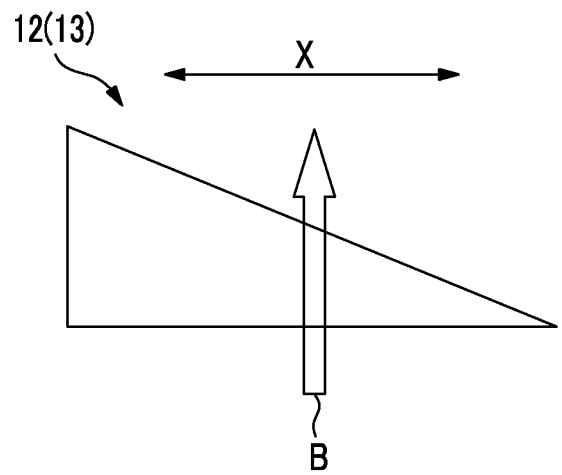

In addition, the plurality of damping material pieces 11 forms a piece group (piece column) 13 arrayed such that the thickness changes sequentially along the first axial direction X (refer to FIGS. 4A and 4B). In the damping unit 12 of the present embodiment, the piece group 13 arrayed in the first axial direction X is formed in a plurality of columns in the second axial direction Y. In addition, in the piece groups 13 adjacent to each other in the second axial direction Y, the damping material pieces 11 are disposed such that the thickness decreases (or increases) in opposite directions.

Figure 3A:
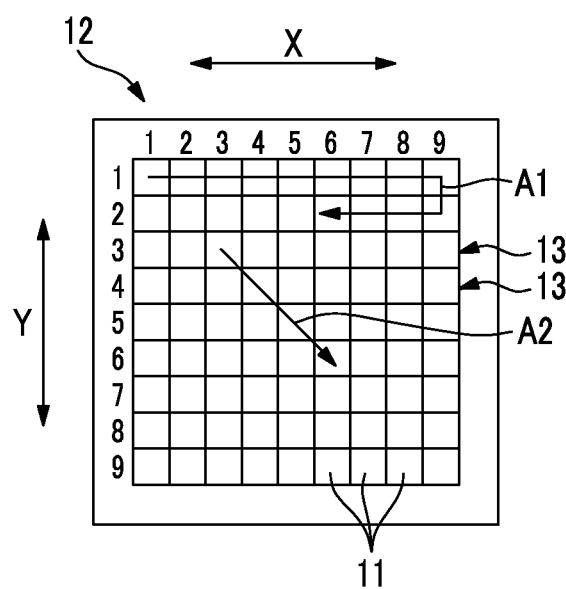
FIGS. 3A and 3B are schematic diagrams showing the arrangement direction of damping material pieces.

Each position of the damping material piece 11 can be expressed using a two-dimensional coordinate system (x, y). For example, the upper left damping material piece 11 shown in FIG. 3A is set as a reference (x, y)=(1, 1), and other damping material pieces 11 are expressed as (2, 1), (3, 1), ..., (9, 1) whenever one movement from the reference (1, 1) is made in the first axial direction X and expressed as (1, 2), (1, 3), ..., (1, 9) whenever one movement from the reference (1, 1) is made in the second axial direction Y. In the damping unit 12 of the present embodiment, the damping material pieces 11 are disposed such that the thickness decreases sequentially whenever the coordinates of the damping material piece 11 move to (1, 1), (2, 1), ..., (9, 1), (9, 2), (8, 2), ..., (1, 2), (1, 3), ..., (9, 9). In addition, the damping material pieces 11 may be disposed such that the thickness increases sequentially, or the damping material pieces 11 may be disposed such that the thickness increases or decreases irregularly. The sequential change in the thickness means that the thickness increases or decreases with a fixed amount of change.

In addition, the damping material piece 11 of the present embodiment has a square shape in front view (when viewed from the traveling direction of the proton beam). In addition, the damping unit 12 that is a group of damping material pieces 11 also has also a square shape in front view. In addition, the shapes of the damping material piece 11 and the damping unit 12 in front view may be other shapes (for example, a triangle, a trapezoid, a rhombus, and a circle).

(Driving Mechanism)

As shown in FIG. 2, the energy degrader 10 includes a driving mechanism (driving unit) 40 that performs translational driving of the damping unit 12 in the first and second axial directions X and Y. The driving mechanism 40 includes: a fixing frame 41 that fixes the damping unit 12; a pair of first linear guides 42 that support the fixing frame 41 from both sides of the first axial direction X; a ball screw 43 for driving the first linear guides 42 in the second axial direction Y; a driving motor 44 for rotationally driving the ball screw 43; a driving frame 45 driven together with the ball screw 43 and the driving motor 44; a pair of second linear guides 46 that support the driving frame 45 from both sides of the second axial direction Y; a ball screw 47 for driving the second linear guides 46 in the first axial direction X; a driving motor 48 for rotationally driving the ball screw 47; and a base frame 49 to which the ball screw 47 and the driving motor 48 are fixed.

The fixing frame 41 is, for example, a rectangular frame body, and fixes a plurality of damping material pieces 11 from the outer surface side. The first linear guide 42 extends in the second axial direction Y, and supports the fixing frame 41 from both sides of the first axial direction X. In addition, a nut 43a into which the ball screw 43 is inserted is connected to the first linear guide 42. In addition, one of the pair of ball screws 43 is connected to the rotary axis of the driving motor 44.

The driving frame 45 is, for example, a rectangular frame body, and supports a pair of ball screws 43 and the driving motor 44. A pair of ball screws 43 are fixed to a frame portion of the driving frame 45, which extends in the second axial direction Y, so as to extend in the second axial direction Y. The second linear guide 46 extends in the first axial direction X, and supports the driving frame 45 from both sides of the second axial direction Y. In addition, a nut 47a into which the ball screw 47 is inserted is connected to the second linear guide 46. In addition, one of the pair of ball screws 47 is connected to the rotary axis of the driving motor 48.

The base frame 49 is, for example, a rectangular frame body, and supports a pair of ball screws 47 and the driving motor 48. A pair of ball screws 47 are fixed to a frame portion of the base frame 49, which extends in the first axial direction X, so as to extend in the first axial direction X.

(Control Unit of Driving Mechanism)

The energy degrader 10 includes a control unit (not shown) that controls the operation of the driving mechanism 40. The control unit of the driving mechanism 40 is provided in a proton beam therapy system control terminal (not shown) that controls the operation of the particle beam therapy system 1, for example. The proton beam therapy system control terminal is configured to include a CPU that performs arithmetic processing, a ROM and a RAM serving as a storage unit, an input signal circuit, an output signal circuit, a power supply circuit, and the like.

The driving motors 44 and 48 are electrically connected to the control unit of the driving mechanism 40. The driving motors 44 and 48 are operated according to a command signal from the control unit. The driving motor 48 drives the driving frame 45 in the first axial direction X. The driving motor 44 drives the fixing frame 41 in the second axial direction Y. That is, the driving frame 45 is driven in the first axial direction X by the driving motor 48 and the ball screw 47, and the fixing frame 41 is driven in the second axial direction Y by the ball screw 43 and the driving motor 44 fixed to the driving frame 45. In this manner, translational driving of the damping unit 12 (a plurality of damping material pieces 11) supported by the fixing frame 41 is performed in the first and second axial directions X and Y.

(Operations of Energy Degrader and Particle Beam Therapy System)

In the particle beam therapy system 1, the proton beam B is accelerated by the cyclotron 2, and the accelerated proton beam B (having an energy range of 230 MeV±several MeV, for example) is introduced into the energy degrader 10. In the energy degrader 10, translational driving of the damping unit 12 in the first and second axial directions X and Y is performed by the driving mechanism 40, and the desired damping material pieces 11 are disposed on the path of the proton beam B. In addition, the proton beam B having passed through the damping material piece 11 is decelerated by the damping material piece 11. As a result, energy is attenuated (for example, 200 MeV±tens of MeV). Here, the energy width of the proton beam B having passed through the damping material piece 11 is slightly increased.

The proton beam B having passed through the energy degrader 10 is introduced into the ESS 30. The ESS 30 extracts the proton beam B of a desired energy range (for example, 200 MeV±1 MeV) selectively among the introduced proton beam B. The proton beam B of the selected energy width is transported through the transport line 4, is introduced into the rotating gantry 3, and is irradiated to an irradiation object. Thus, the proton beam B is irradiated so as to reach a predetermined depth-direction position inside the irradiation object.

According to the energy degrader and the particle beam therapy system including the energy degrader of the present embodiment, a damping unit having a thickness changing stepwise or continuously (linearly or in a curved manner) is disposed in a two-dimensional manner on the plane crossing the traveling direction of charged particles. In addition, since the energy degrader is configured to include a driving unit that performs translational driving of the damping unit in the first and second axial directions crossing each other in the two-dimensional coordinate system, it is possible to reduce the maximum size of the appearance of the damping unit compared with a method of driving the damping unit in one axial direction. As a result, it is possible to reduce the size of the device. In addition, since the movement time is shortened by moving the damping unit in the two axial directions simultaneously, it is possible to shorten the adjustment time of the energy attenuation.

In addition, in the damping unit 12 of the energy degrader 10 of the present embodiment, the piece group 13 is provided in which a plurality of damping material pieces 11 are disposed such that the thickness changes sequentially along the first axial direction, the piece group 13 is formed in a plurality of columns in the second axial direction Y, and the piece groups 13 adjacent to each other in the second axial direction Y are disposed such that the thickness decreases in opposite directions. For example, the damping material pieces 11 are arrayed such that the thickness decreases whenever movement in the right direction in the drawing is made in the piece group 13 in the odd column and the thickness decreases whenever movement in the left direction in the drawing is made in the piece group 13 in the even column. Thus, since the plurality of damping material pieces 11 are disposed such that the thickness changes sequentially, it is possible to suppress the moving distance of the damping unit 12 short. Accordingly, it is possible to shorten the adjustment time of the energy attenuation.

In addition, in the particle beam therapy system of the present embodiment, the energy degrader 10 is disposed between the cyclotron 2 and the ESS 30. Accordingly, the proton beam B having desired energy width can be selectively extracted from the proton beam B having passed through the energy degrader 10 by the ESS 30. The energy width of the proton beam B is increased when the proton beam B passes through the energy degrader 10, but the proton beam B of a desired energy range is selectively extracted by the ESS 30 thereafter. Therefore, the energy width of the proton beam B transported to the rotating gantry 3 can be accurately adjusted. In addition, the energy degrader 10 may be provided after the ESS 30.

Figure 3B:
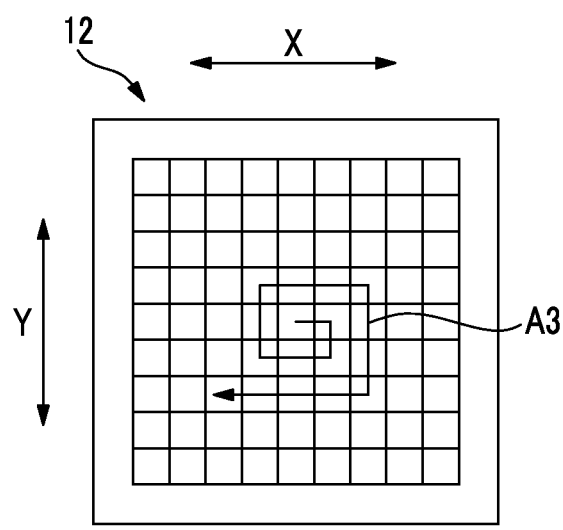

While the present invention has been specifically described on the basis of the embodiment, the present invention is not limited to the above embodiment. FIGS. 3A and 3B are schematic diagrams showing the arrangement direction of damping material pieces. In the embodiment described above, the damping unit 12 is configured such that the thickness of the damping material piece 11 decreases as indicated by the arrow A1 in FIG. 3A. However, the damping material pieces 11 may be disposed such that the thickness decreases along the other directions. For example, the damping material pieces 11 may be disposed such that the thickness decreases or increases sequentially in the diagonal direction indicated by the arrow A2 in FIG. 3A. In addition, as indicated by the arrow A3 in FIG. 3B, the damping material pieces 11 may be disposed such that the thickness decreases or increases sequentially in a spiral shape with the center of the damping unit 12 as the base.

FIGS. 4A and 4B are side views showing the shape of a damping unit in the thickness direction. In the embodiment described above, as shown in FIG. 4A, the damping unit 12 is configured such that the thickness changes stepwise. However, as shown in FIG. 4B, the damping unit 12 may be configured such that the thickness changes linearly (continuously), for example, according to the position in the first axial direction X. In addition, the damping unit may be configured such that the thickness changes in a curved manner. For example, the rate of change in the thickness may not be constant.

In addition, although the damping unit 12 described above is formed of a group of the plurality of damping material pieces 11, the damping unit 12 may be integrally formed in such a manner that the thickness changes according to the position. In addition, the damping unit 12 may be integrally formed, for example, for each portion extending in the first axial direction X.

In addition, the energy degrader 10 may be configured to include a damping unit, in which the thickness changes stepwise according to the position of the two-dimensional coordinate system within the plane crossing the traveling direction of charged particles, and a driving unit, which rotationally drives the damping unit around the rotary axis extending in the traveling direction and drives the damping unit in a radial direction of a circle having the rotary axis as the center, in an energy degrader including a damping unit that attenuates the energy of incident charged particles. Thus, since it is possible to reduce the maximum size of the appearance of the damping unit compared with a method of driving the damping unit in one axial direction, it is possible to reduce the size of the device. In such a case, it is possible to form a driving unit that moves a damping unit in a radial direction by moving the rotary axis in a predetermined direction.

Here, it is preferable to adopt a configuration in which the damping unit 12 is a group of the plurality of damping material pieces 11 having different thicknesses, the group includes a piece column in which the plurality of damping material pieces 11 are disposed such that the thickness changes sequentially along the circumferential direction of a circle, and the plurality of piece columns are formed in the radial direction so as to be disposed in a spiral shape having the rotary axis as the center. Thus, since the plurality of damping material pieces 11 are disposed such that the thickness changes sequentially, it is possible to shorten the adjustment time of the energy attenuation by shortening the moving distance of the damping unit 12. In addition, it is also possible to configure a charged particle irradiation system including such an energy degrader.

In addition, the charged particles are not limited to the proton beam using hydrogen, and may be other charged particles (for example, heavy ion beam using carbon).

In addition, the accelerator is not limited to the cyclotron, and may be other accelerators (for example, a synchrocyclotron or a synchrotron).

In addition, the energy degrader is not limited to being disposed between the cyclotron and the ESS, and may be disposed in other places (for example, inside the irradiation nozzle provided in the rotating gantry).

In addition, the charged particle irradiation system may not include the energy selection unit. The charged particle irradiation system may have a configuration in which an energy degrader is provided and charged particles, of which energy has been attenuated by the energy degrader, can be irradiated.

In the energy degrader and the charged particle irradiation system including the energy degrader according to the embodiment of the present invention, it is possible to reduce the maximum size of the appearance of the damping unit. Therefore, it is possible to reduce the size of the device.

It should be understood that the invention is not limited to the above-described embodiment, but may be modified into various forms on the basis of the spirit of the invention. Additionally, the modifications are included in the scope of the invention.

What is claimed is:

1. An energy degrader, comprising:
   a damping unit that attenuates energy of incident charged particles and has a thickness changing stepwise or continuously according to a position of a two-dimensional coordinate system within a plane crossing a traveling direction of charged particles; and
   a driving unit that performs translational driving of the damping unit in first and second axial directions that are directions of two axes crossing each other in the two-dimensional coordinate system.

2. The energy degrader according to claim 1,
   wherein directions of two axes perpendicular to each other in the two-dimensional coordinate system are set as the first and second axial directions,
   the damping unit is a group of a plurality of pieces having different thicknesses,
   the group includes a piece column in which the plurality of pieces are disposed such that the thickness changes sequentially along the first axial direction, and
   the plurality of pieces are disposed such that the thickness changes sequentially in opposite directions between the adjacent piece columns.

3. A charged particle irradiation system that irradiates charged particles, comprising:
   the energy degrader according to claim 1.

4. The charged particle irradiation system according to claim 3, further comprising:
   an accelerator that is disposed before the energy degrader and accelerates the charged particles;
   an energy selection unit that is disposed after the energy degrader and extracts charged particles of desired energy width selectively from the charged particles having passed through the energy degrader; and
   an irradiation device that is disposed after the energy selection unit and irradiates the charged particles of the desired energy width extracted by the energy selection unit.

5. A charged particle irradiation system that irradiates charged particles, comprising:
   the energy degrader according to claim 2.

* * * * *